United States Patent
Samouilhan et al.

[11] Patent Number: 6,162,486
[45] Date of Patent: Dec. 19, 2000

[54] PROCESS FOR ACQUIRING FINGERPRINTS AND DEVICE FOR IMPLEMENTING THIS PROCESS

[75] Inventors: Stéphane Samouilhan, Paris, France; Henri Rajbenbach, Brussels, Belgium; Claude Bricot, Villejuif, France

[73] Assignee: Thomson-CSF, Paris, France

[21] Appl. No.: 09/077,314

[22] PCT Filed: Oct. 6, 1997

[86] PCT No.: PCT/FR97/01778

§ 371 Date: Sep. 18, 1998

§ 102(e) Date: Sep. 18, 1998

[87] PCT Pub. No.: WO98/15225

PCT Pub. Date: Apr. 16, 1998

[30] Foreign Application Priority Data

Oct. 4, 1996 [FR] France ................................ 96 12127

[51] Int. Cl.⁷ .................................................... A61B 5/117
[52] U.S. Cl. .............................. 427/1; 427/428; 118/31.5
[58] Field of Search ........................ 427/1, 428; 118/31.5

[56] References Cited

U.S. PATENT DOCUMENTS 3,804,524  4/1974  Jocoy et al. .
3,824,951  7/1974  Le Vantine et al. .
4,706,600  11/1987  Mason, Jr. et al. ......................... 427/1
5,599,391  2/1997  Lee .

OTHER PUBLICATIONS

"How things work", Granada Publishing Limited, St. Albans and London (GB), vol.1, (1980), XP002033261, pp. 418–419.

*Primary Examiner*—Shrive Beck
*Assistant Examiner*—Kirsten A. Crockford
*Attorney, Agent, or Firm*—Oblon, Spivak, McClelland, Maier & Neustadt, P.C.

[57] ABSTRACT

Process for acquiring fingerprints, characterized in that it comprises the following steps:
 coating, with the aid of an ink, the surfaces of the fingers of a hand whose prints are to acquired;
 pressing a pad (2) of flexible material against the said coated surfaces;
 pressing the pad against a recording support (3). According to this process, the print is therefore taken on an intermediate pad and subsequently transferred to a paper support.

14 Claims, 9 Drawing Sheets

PROCESS FOR ACQUIRING FINGERPRINTS AND DEVICE FOR IMPLEMENTING THIS PROCESS

The invention relates to a process for acquiring fingerprints and to a device for implementing this process.

This invention therefore relates to the field of fingerprint acquisition. It makes it possible to acquire one or more prints simultaneously.

This method makes it possible to acquire prints with reproducibility of print acquisition.

Within the field, there are conventionally two types of fingerprint acquisition devices:

1) Inking pads: the individual places his finger on an inking pad then applies it to a sheet of paper so as to transfer the image of the ridges and furrows.
2) Acquisition by a camera: these devices use the principle of the frustrated total internal reflection of a light wave illuminating an optical dioptre lens (see references 1 and 2 at the end of the description). The person applies his finger to an optical prism consisting of a block of glass. The points of the finger in contact with the prisms (the ridges of the print) perturb the coefficient of reflection by perturbing the index in the vicinity of the interface dioptre lens. The image of the dioptre lens is transmitted to a camera (generally a CCD video camera) which thus records the fingerprint.

The main drawbacks of these devices are the quality, and especially the reproducibility of the acquisition. This second point would appear to be a major problem if it is desired to automate the operations of identification (population monitoring) and authentication (access control) (see references 3, 4 and 5 at the end of the description).

Another drawback of the second device is the cost of the system.

The present patent application proposes to improve the quality of the image (uniform distribution of ink over the finger) and especially the reproducibility of acquisition without a corresponding significant increase in the costs or acquisition time as compared with the conventional method of acquisition with an inking pad. This new process for acquiring fingerprints is based on the passivity of the candidate while the print is being taken in order to solve the acquisition repeatability problem. The flexibility of the plastic which is used makes it possible to carry out an equivalent acquisition in terms of area acquired when the finger is "rolled" over an inking pad, while also ensuring the passivity of the candidate. The device is described below in detail.

The invention therefore relates to a process for acquiring fingerprints, characterized in that it comprises the following steps:

coating, with the aid of an ink, the surfaces of the fingers of a hand whose prints are to be acquired;

pressing a pad of flexible material against the said coated surfaces;

pressing the pad against a recording support.

The invention also relates to a device for acquiring fingerprints, characterized in that it comprises:

a support piece possessing a face intended to receive at least one finger or hand whose print it is desired to acquire, or alternatively a recording support;

a pad made of flexible material;

a system for guiding the pad perpendicular to the face.

The various subjects and characteristics of the invention will emerge more clearly from the description which follows and the appended Figures, in which:

FIGS. 2a to 2d represent a support plate and its mode of use;

The process for acquiring prints according to the invention will be described while referring to FIGS. 1a to 1d.

Figure 1A:
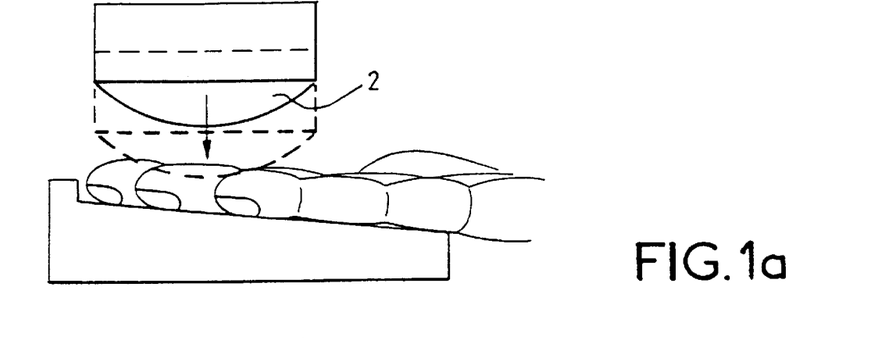
FIGS. 1a to 1c represent various steps of the process according to the invention.
Figure 1B:
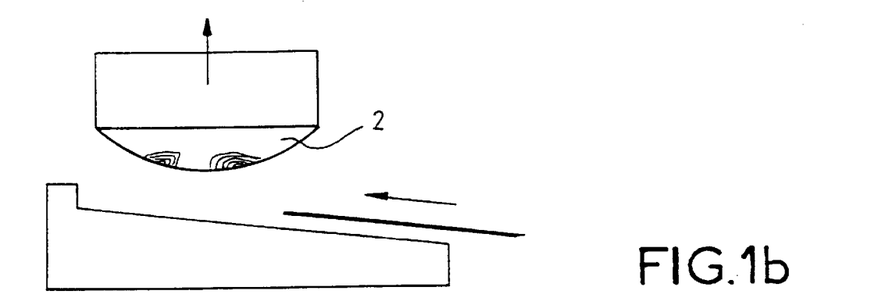
Figure 1C:
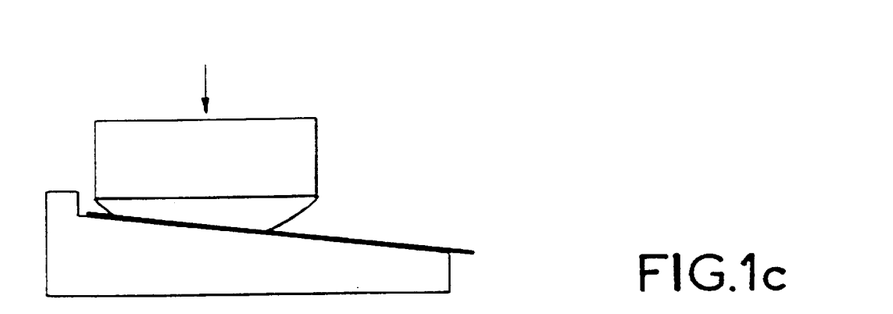
Figure 1D:
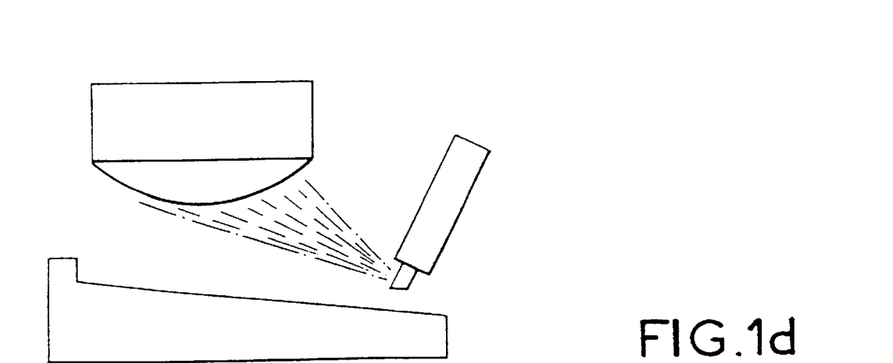

In general, this process provides for the following main steps:

the faces of the fingers whose prints are to be acquired are coated with an ink;

subsequently, as represented in FIG. 1a, a pad of flexible material is applied against the faces of the fingers. The surface of the pad is made of a material capable of taking up the ink deposited on the fingers;

the hand is removed and a recording support such as a sheet of paper is set in place of the hand (FIG. 1b);

the pad is set in contact with the sheet of paper (FIG. 1c) and transfers the image of the fingerprints onto the sheet of paper;

the pad is then cleaned (FIG. 1b) to remove the ink from its surface so as to use it for a subsequent acquisition.

This cleaning can be done, for example, by spraying a solvent.

In this process, the finger or fingers whose prints are acquired have to be wedged. A support is therefore provided which, for example, takes the form of a plate 1. The face 10 of this plate possesses means for wedging the fingers.

Figure 2A:
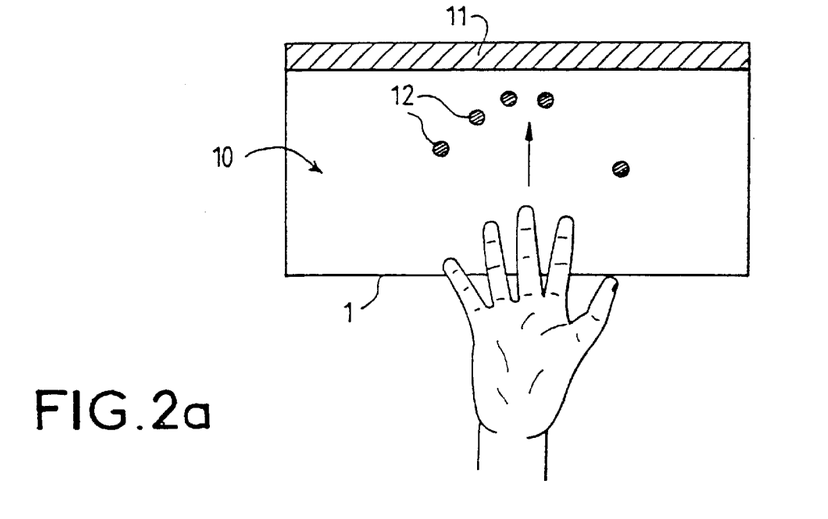
Figure 2B:
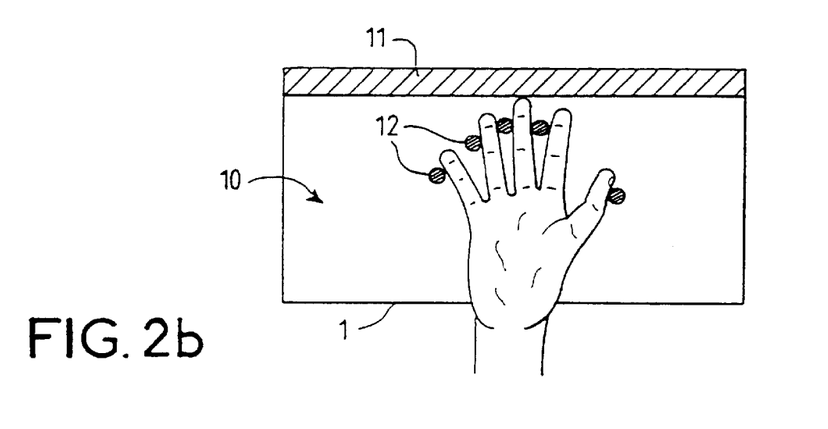
Figure 2C:
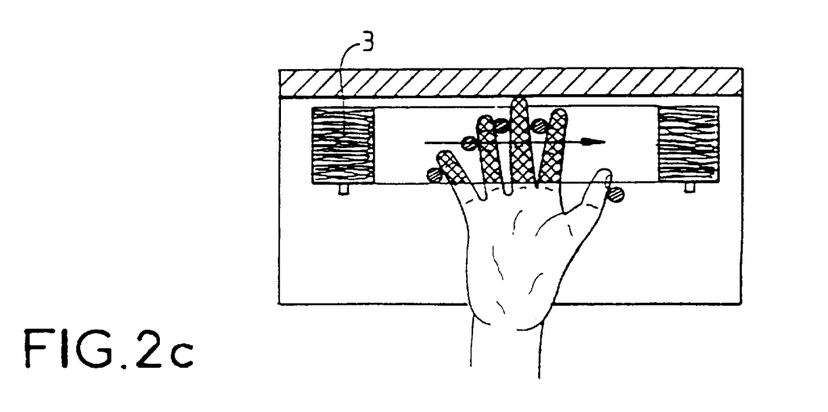

According to FIGS. 2a to 2c, the face 10 possesses a stop 11 which limits the axial displacement of the fingers, and stops such as 12 which are designed to be located on either side of the fingers and which limit the lateral displacement of the fingers. As represented in FIG. 2a, a hand is brought near to the support 1, the back of the hand being on the face 10. The fingers are placed between the stops 12, and the middle finger abuts against the stop 11 (FIG. 2b). An ink coating device, such an ink roller 3, is passed over the faces of the fingers whose prints are to be acquired by movement over the hand (FIG. 2c). The device is then ready for acquisition of the prints.

The more complete process for acquiring fingerprints according to the invention can be described as follows:

Step 1 (FIG. 2a): the candidate for acquisition places his hand with the outside face on the support 1 of the device (plan view of the right hand);

Step 2: A check must be made to verify that each of the fingers is correctly positioned with respect to the stops. The purpose is to position the hand in a repetitive manner;

Step 3: Automatic inking of the 4 fingers (forefinger, middle finger, ring finger, little finger) with the aid of a spray, a roller etc. Here again the purpose is to control the repeatability of this step;

Step 4: Lowering of the flexible plastic pad 2 while controlling the pressure on the fingers;

Step 5: Raising of the flexible pad. Next, the candidate removes his hand. A paper form is inserted and abutted on the device;

Step 6: Lowering of the pad with control of pressure on the paper form. The prints of the 4 fingers of the candidate are therefore recovered on a paper support;

Step 7: Cleaning of the plastic pad with the aid of a solvent spray.

FIGS. 3a to 3f represent an embodiment of the apparatus for taking prints according to the invention. This apparatus comprises (see FIG. 3a) a support plate 1 which is similar to that of FIGS. 1a to 1c and is intended to receive a hand whose print is to be acquired.

Figure 3A:
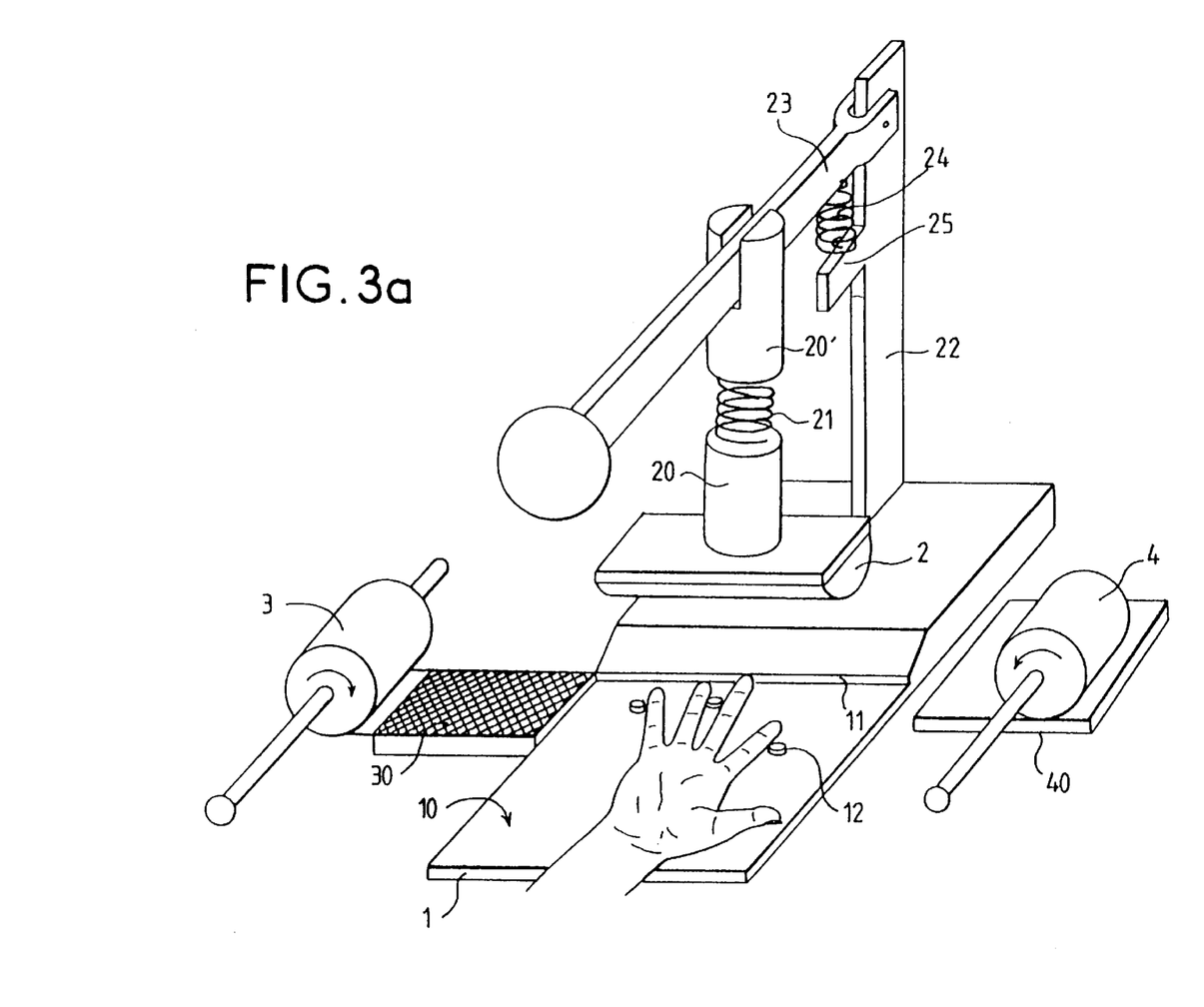
FIGS. 3a to 3h represent an apparatus for taking prints according to the invention.

The pad 2 is located above the face 10 of the plate 1. This pad is secured to a shaft 20 which can move vertically under the action of a lever 23 articulated on a post 22 fixed to the plate 1. By actuating the lever 23, the pad 2 can be set in contact with the plate 2 (or with the hand placed on the plate).

The travel of the lever 23 is limited, for example, by the stop 25 and the spring 24. A spring 21 is interposed between the shaft 20 of the pad 2 and the lever 23. The spring 21 is held in place by, for example, sliding the shaft 20 within a shaft 20' secured to the lever 23. The spring 21 thus enables a constant pressure to be exerted on the pad.

A reserve of ink 30 of the inking pad type is provided on the left part of the apparatus. An inking roller 3 can roll over this inking pad in order to become charged with ink.

A cleaning roller 4 with a cleaning device 40 of the cleaning vessel type comprising a solvent, for example, is provided on the right part.

This apparatus operates as follows.

In FIG. 3a, the "patient" places his hand on the support plate 1. The hand is positioned by the stops 12.

Figure 3B:
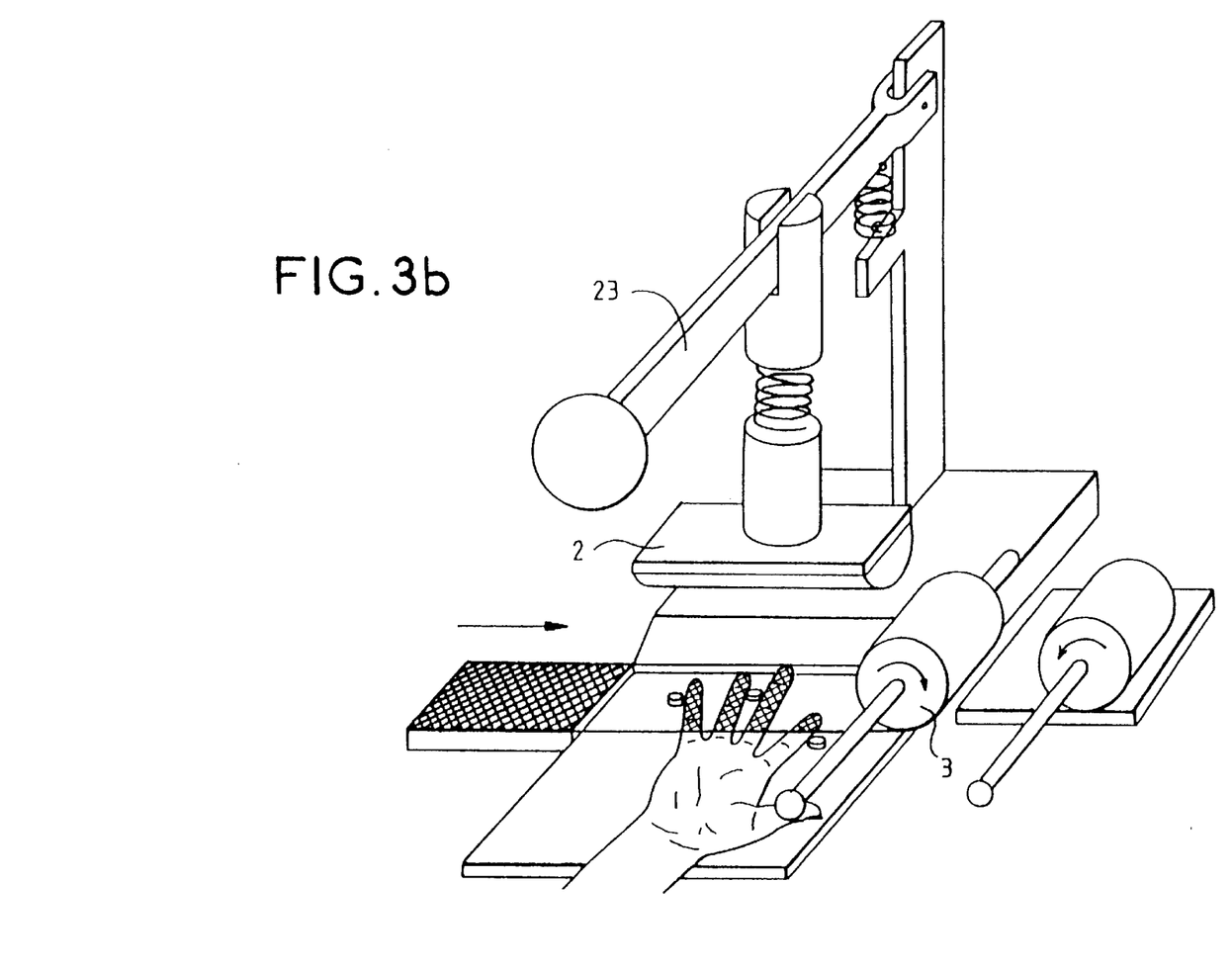

In FIG. 3b, the inking roller 3 charged with ink is moved over the hand and coats it with ink.

Figure 3C:
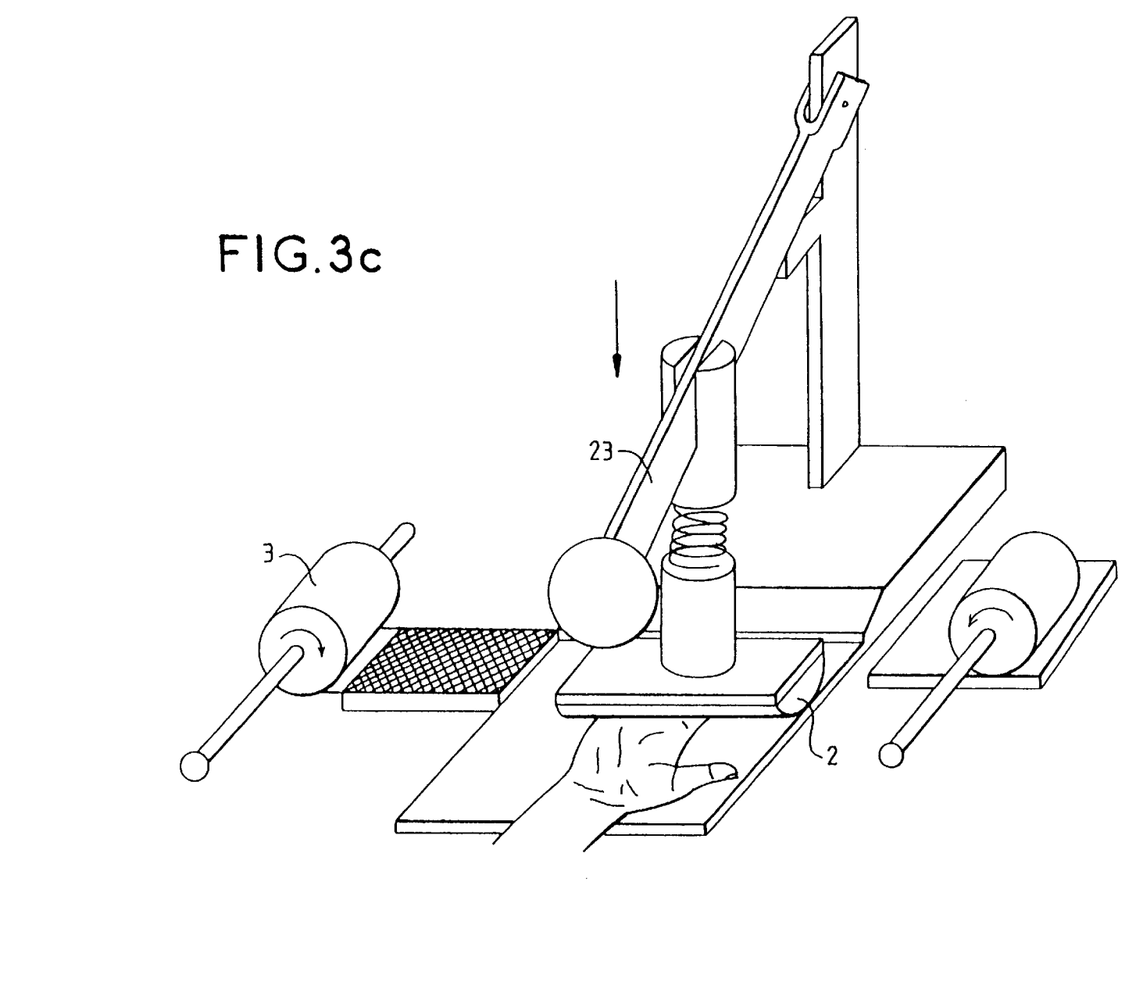

In FIG. 3c, the lever 23 is lowered and the pad 2 presses the ink-coated hand lightly. The prints of the hand are printed on the pad 2.

Figure 3D:
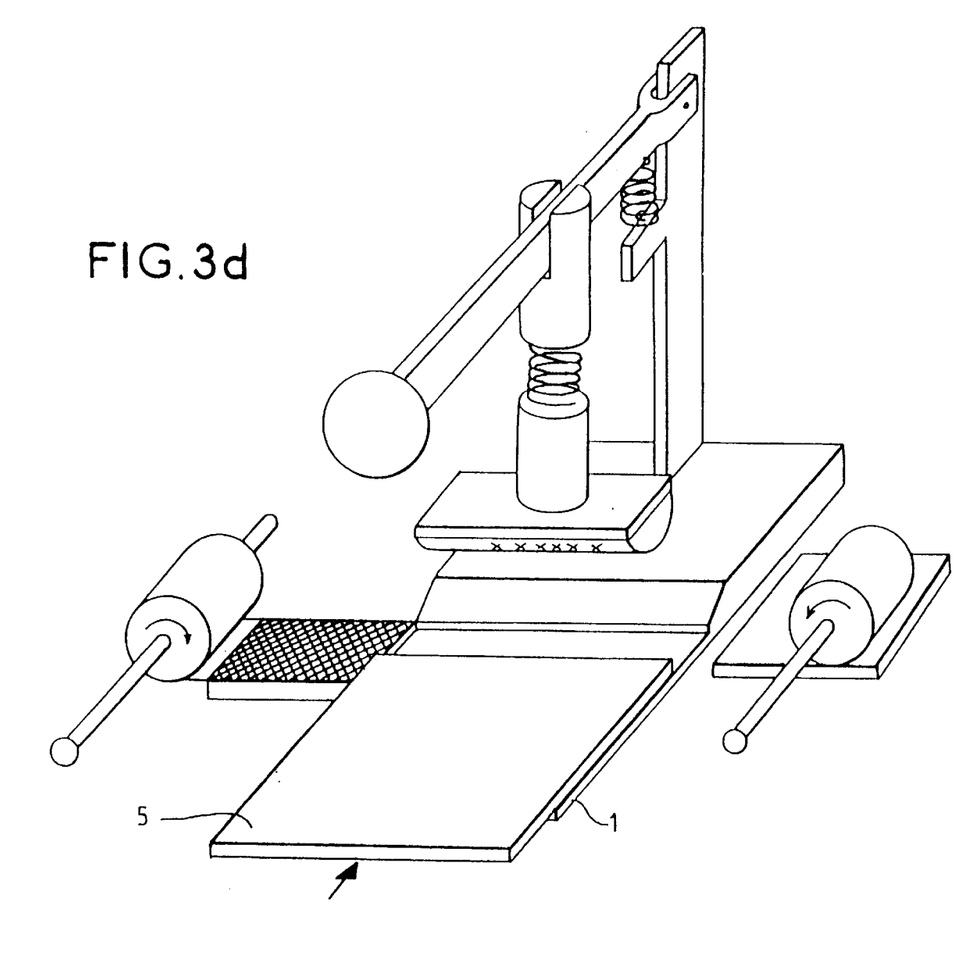
Figure 3E:
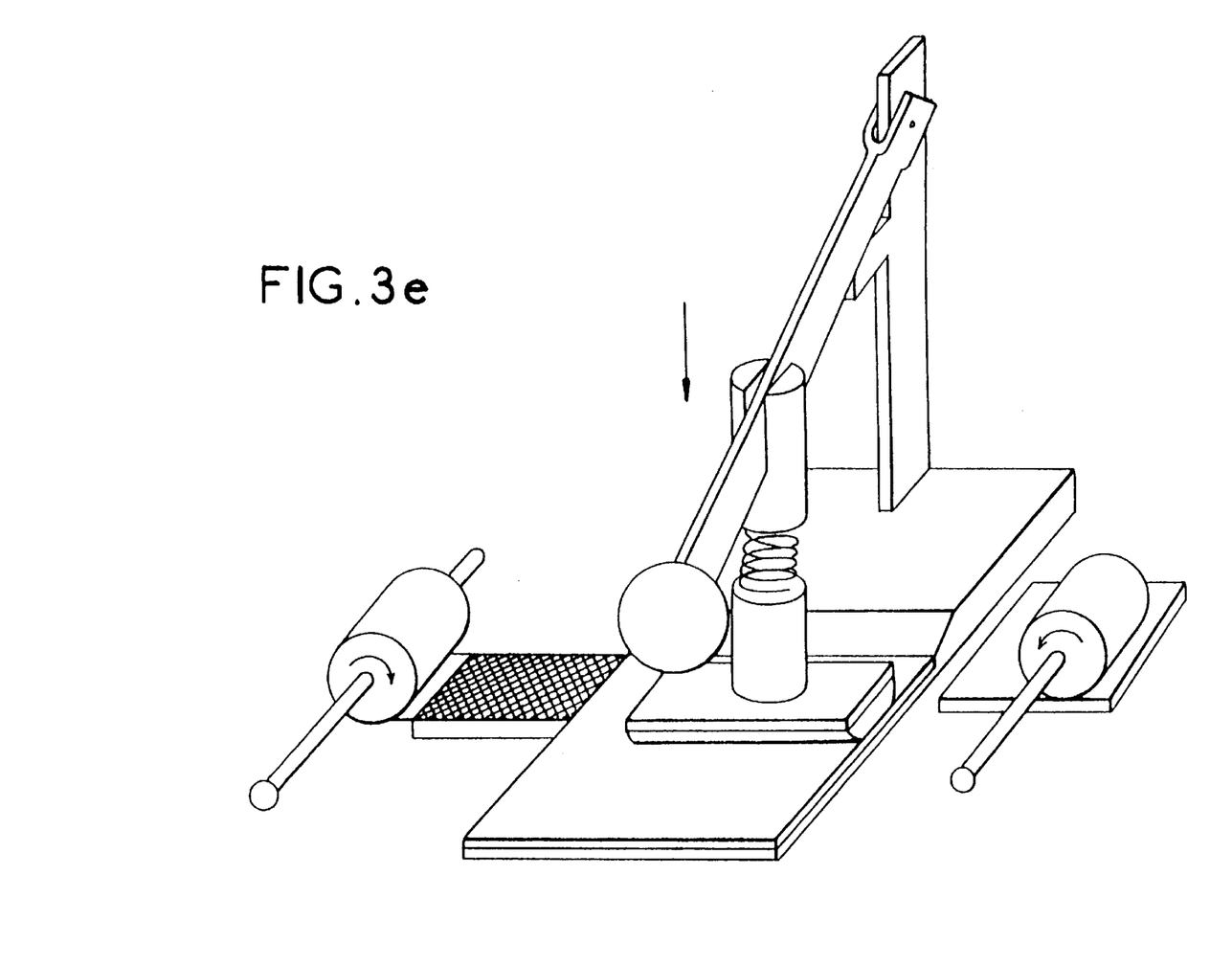

In FIG. 3d, the lever 23 and the pad 2 are raised. The patient has raised his hand. A moveable tray 1' is placed on the face 10 of the plate 1 and fits over the stops 12 in such a way that the latter do not emerge from the upper surface of the plate 1'. A sheet of paper 5 is then placed on the movable tray 1' and a sheet of paper 5 has been placed on the face.

In FIG. 3e, the lever 23 is again lowered and the pad 2 is pressed against the sheet of paper. The print printed on the paper is transferred to the paper 5.

Figure 3F:
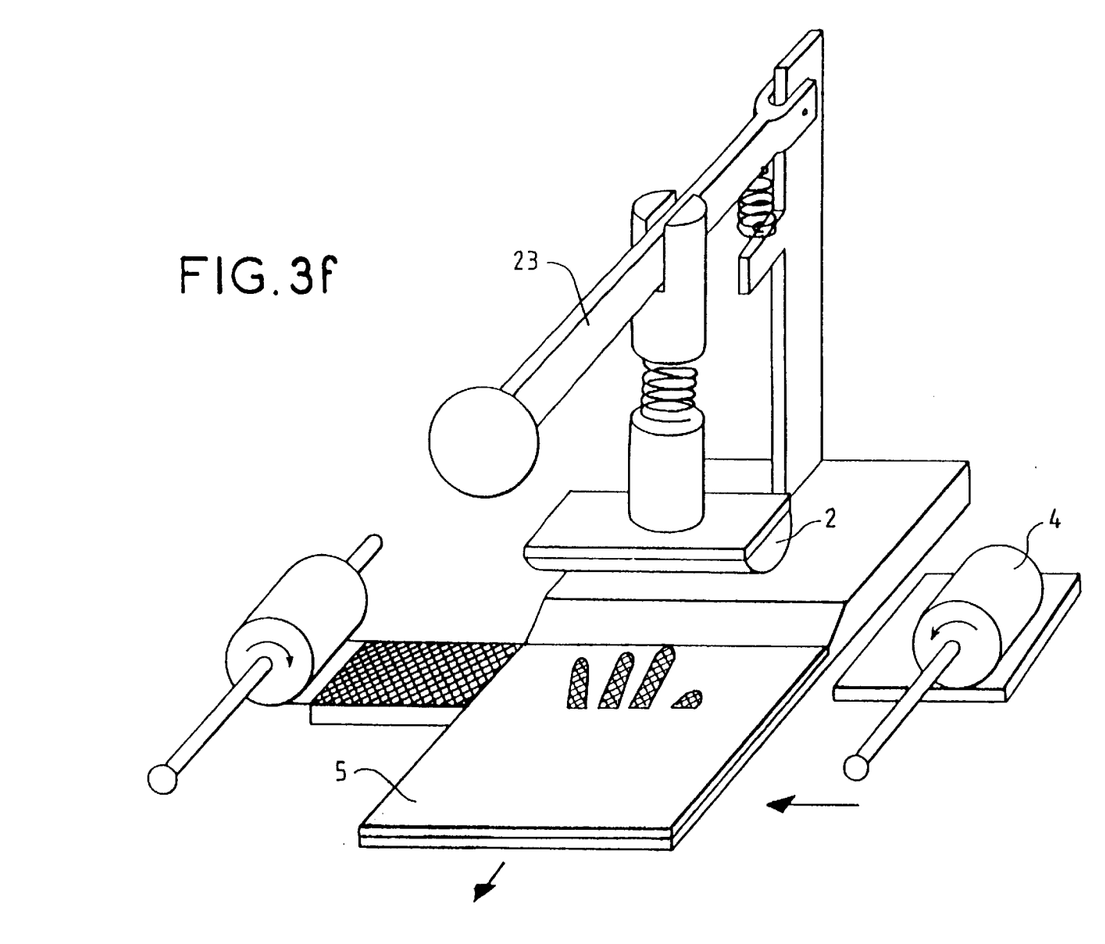

In FIG. 3f, the lever is raised together with the pad 2. The paper 5 bearing the prints of the hand can be removed. The pad 4 is moved under the pad 2 in order to eliminate the traces of ink resulting from having just taken prints.

Figure 3G:
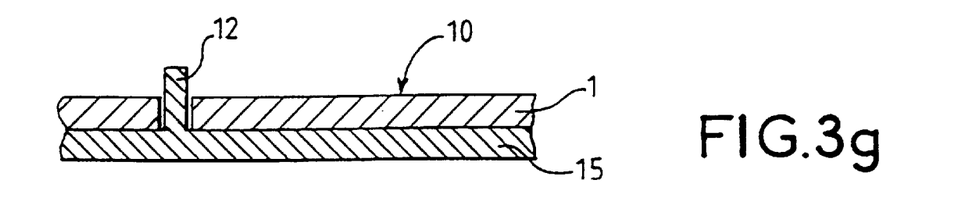
Figure 3H:
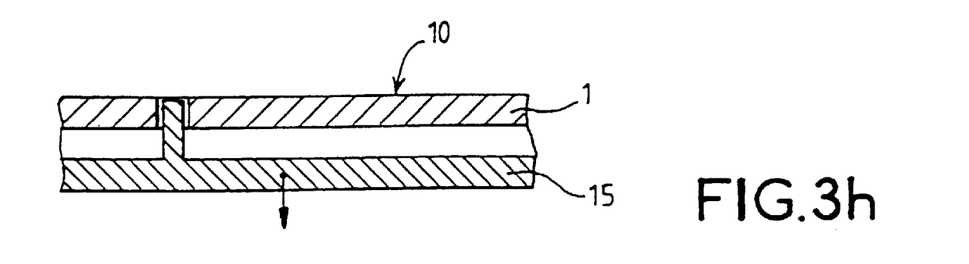

According to a variant embodiment, to allow the sheet of paper 5 to be laid directly on the face 10 of the support plate 1 without the stops 12 being in the way, there is provision for the stops to be secured to a moveable plate 16 placed under the support plate (FIG. 3g). This plate 16 is provided with stops 12 whose height is greater than the thickness of the plate 1. When the hand is to be placed on the face 10, the moveable plate 16 is pushed against the lower face of the support plate 1 and the stops emerge from the face 10. When the hand is removed and a sheet of paper 5 is to be put in place, with the aid of a lever system (not represented), the moveable plate 15 is separated from the support plate 1 so that the stops 12 retreat into the support plate 1 (FIG. 3h).

EXAMPLE OF AN IMPLEMENTATION

Device for inking the fingers:
conventional inking pad;
spray;
roller.
Flexible plastic pad (T):
Flexible plastics: material used in pad technology relating to nonplanar surfaces, for example. In these diagrams, the manner in which the plate 1 may serve as support for the sheet of paper should also be shown. To do this, the stops 12 could be designed so as to "retreat" into the plate 1 (make diagrams).

Device for cleaning the plastic pad:
Use of a solvent spray suitable for the flexible plastic.
According to variants of the invention:
it is possible to modify the support (S) in such a way as to carry out acquisition of one finger or a pair of fingers. A finger guide shall have to be set in place in order to ensure the repeatability of acquisition;
the support (S) can be placed horizontally or, more ergonomically, vertically or inclined. In this case, the person will lay the back of his hand against this support provided with a positioning guide.

The invention has the following advantages:
Acquisition of fingerprints with improved image quality by comparison with the methods with inking pads.
Repeatability of acquisition, allowing better processing of the prints with a view to identification or authentication.

The pad 2 possesses a flexible material which makes it possible to take on the shape of the finger (or fingers) and whose surface condition allows the ink from the finger to be transferred to the pad. Subsequently, the pad returns to shape and when it is applied to the sheet of paper, the ink from the pad is transferred to the sheet of paper. By way of example, the material may be a material used for the inking pads for printing on nonplanar surfaces, made of silicone for example such as a silicone marketed by the company SOTRAS (OYONNAX-France). The pad may also be made of an inflatable elastic material. The ink may be a liquid, pasty or powdered material.

The process makes it possible to obtain a print area equivalent to that obtained when a finger is rolled with an inking pad. This area makes it possible to calculate the Galton number, something which is not possible during print acquisition with a camera.

Cost of the system less than the method of acquisition by a camera.

What is claimed is:

1. A process for acquiring fingerprints, comprising the steps of:
coating an ink on the surfaces of the fingers of a hand whose prints are to be acquired;
pressing a pad of flexible material against said coated surfaces;
pressing the pad against a recording support and
removing the pad from the recording support to transfer the fingerprint to the recording support.

2. The process according to claim 1, further comprising the steps of:
before or after coating the surfaces of the fingers, placing the hand on a support with the back of the hand against a face of the support;
setting said pad in contact with the surfaces of the fingers under a specified pressure;
removing the hand from the support and replacing the hand with the recording support; and
setting said pad in contact with the recording support under a specified pressure.

3. The process according to claim 1, wherein said support is made of a flexible plastic.

4. The process according to claim 1, wherein said surfaces of the fingers are coated with an ink by at least one of setting the surfaces of the fingers in contact with an inking pad, spraying the surfaces with said ink and passing an ink-coated roller over said surfaces.

5. A device for acquiring fingerprints, comprising:

a support piece including a face configured to receive successively at least one finger or hand whose print is desired to be acquired and a recording support;

a pad made of flexible material capable of accepting an ink fingerprint image from a finger and of transferring the image from the pad to a recording support to record the ink fingerprint image; and a system for guiding the pad perpendicular to the face.

6. The device according to claim 5, wherein said face of the support piece comprises means for wedging the finger or fingers of the hand.

7. The device according to claim 6, wherein said wedging means comprises stops which are intended to be located between the fingers and to wedge the fingers laterally.

8. The device according to claim 7, wherein said stops can be retracted into the support.

9. The device according to claim 6, wherein said wedging means comprises a stop which limits the axial displacement of the finger.

10. The device according to claim 5, wherein said guide system comprises a lever which controls the vertical displacement of the pad, as well as a stop which limits the travel of the lever.

11. The device according to claim 5, wherein said guide system comprises a spring interposed between the pad and the lever.

12. The device according to claim 8, wherein said stops are secured to a removable plate located under the support plate, the stops having a height greater than the thickness of the support plate and passing through the support plate via holes.

13. The device according to claim 5, wherein said pad is made from a deformable material having the property of returning to its original shape after deformation.

14. The device according to claim 13, wherein said pad is made of a silicone-based material.

* * * * *